(12) United States Patent
Al Ahmad

(10) Patent No.: US 10,416,093 B2
(45) Date of Patent: Sep. 17, 2019

(54) METHOD AND SYSTEM FOR CHARACTERIZATION OF MICROALGAL LIPID CONTENT

(71) Applicant: United Arab Emirates University, Al Ain (AE)

(72) Inventor: Mahmoud F. Y. Al Ahmad, Al Ain (AE)

(73) Assignee: United Arab Emirates University, Al Ain (AE)

(*) Notice: Subject to any disclaimer, the term of this patent is extended or adjusted under 35 U.S.C. 154(b) by 195 days.

(21) Appl. No.: 15/121,647

(22) PCT Filed: May 25, 2015

(86) PCT No.: PCT/IB2015/053861
§ 371 (c)(1),
(2) Date: Aug. 25, 2016

(87) PCT Pub. No.: WO2015/181702
PCT Pub. Date: Dec. 3, 2015

(65) Prior Publication Data
US 2018/0188237 A1 Jul. 5, 2018

Related U.S. Application Data

(60) Provisional application No. 62/002,883, filed on May 25, 2014.

(51) Int. Cl.
*G01N 22/00* (2006.01)
*G01N 29/36* (2006.01)
(Continued)

(52) U.S. Cl.
CPC ............... *G01N 22/00* (2013.01); *C12N 1/12* (2013.01); *C12N 1/26* (2013.01); *G01N 29/00* (2013.01);
(Continued)

(58) Field of Classification Search
None
See application file for complete search history.

(56) References Cited

FOREIGN PATENT DOCUMENTS

| JP | 2002071585 A | 3/2002 |
|---|---|---|
| JP | 2007271412 A | 10/2007 |

(Continued)

OTHER PUBLICATIONS

International Search Report, International Patent Application No. PCT/IB2015/053861, dated Aug. 13, 2015, 4 pages.
(Continued)

*Primary Examiner* — Olivia M. Wise
(74) *Attorney, Agent, or Firm* — Fitch, Even, Tabin & Flannery LLP

(57) ABSTRACT

Method and system (100) for characterizing lipid content in microalgae are disclosed. An input signal is transmitted to a resonator cavity (102) containing a sample microalgal suspension and a frequency response curve is obtained. Subsequently, a set of sample parameters is determined based on a Gaussian distribution modelling of the frequency response curve. An amount of lipid content in the sample microalgal suspension is determined based on correlation between the sample parameters and a set of reference parameters, wherein the reference parameters correspond to specific amounts of lipid content.

20 Claims, 8 Drawing Sheets

(51) Int. Cl.
G01N 29/00 (2006.01)
G01N 29/44 (2006.01)
C12N 1/12 (2006.01)
C12N 1/26 (2006.01)

(52) U.S. Cl.
CPC ......... *G01N 29/36* (2013.01); *G01N 29/4418* (2013.01); *G01N 29/4427* (2013.01)

(56) References Cited

FOREIGN PATENT DOCUMENTS

RU 2192646 C1 11/2002
WO 2014/076506 A1 5/2014

OTHER PUBLICATIONS

Written Opinion of the International Searching Authority, International Patent Application No. PCT/IB2015/053861, dated Aug. 13, 2015, 4 pages.

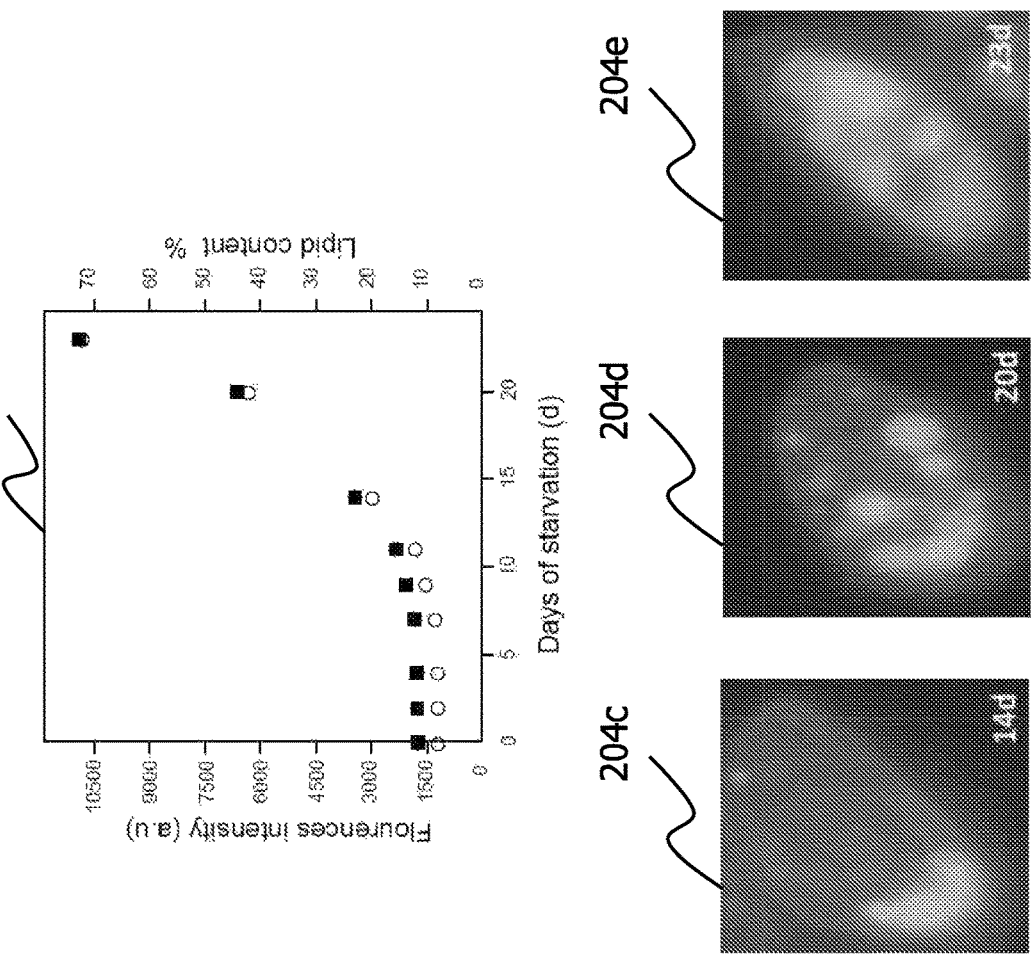
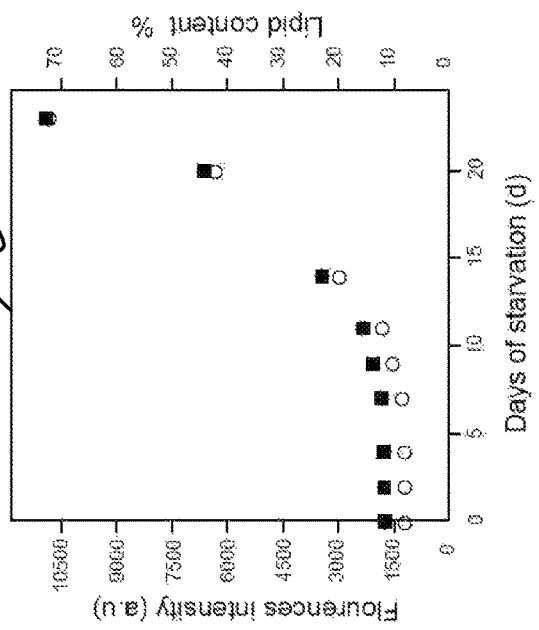
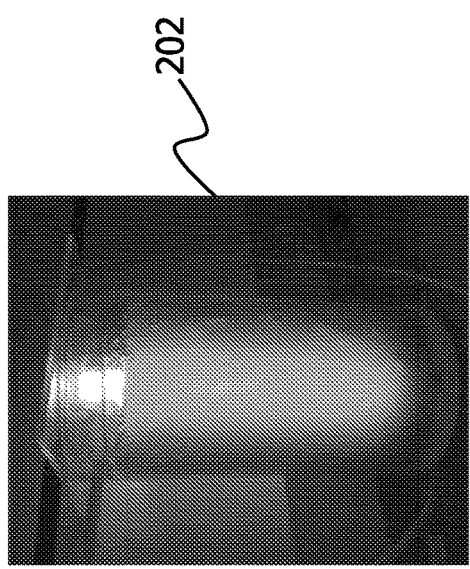

| Prediction Coefficients | | | | | |
|---|---|---|---|---|---|
| Days | Lipid (%) | $y_o$ | A | $f_o$ | w |
| 0 | 0 | -1.034 | -3.848 | 11.896 | 0.593 |
| 2 | 11.74 | -0.974 | -3.461 | 11.897 | 0.643 |
| 11 | 15.50 | -0.962 | -3.370 | 11.901 | 0.648 |
| 14 | 22.93 | -0.938 | -3.219 | 11.911 | 0.654 |
| 20 | 44.52 | -0.871 | -2.843 | 11.939 | 0.668 |
| 23 | 73.27 | -0.755 | -2.326 | 11.978 | 0.696 |

FIG 6

METHOD AND SYSTEM FOR CHARACTERIZATION OF MICROALGAL LIPID CONTENT

BACKGROUND OF THE PRESENT INVENTION

Technical Field

The present invention relates to microalgal lipid content characterization and more particularly, to a method and a system for radio frequency based characterization of microalgal lipid content.

Description of the Related Art

Biofuel, including biodiesel and other biohydrocarbons, produced from microalgal lipids is considered to be a promising alternative to fossil fuels. To achieve commercially viable biodiesel production from microalgae, high biomass and high lipid content are required. However, the conditions favouring high biomass productivity usually result in low lipid accumulation, and vice versa. Under stress conditions, as growth rate drops, microalgae tend to accumulate larger lipid content. Thus, the requirements of high biomass and high lipid content are inherently contradictory and entail diligent optimisation of process conditions. To achieve this, it is essential to be able to monitor lipid accumulation.

Several techniques have been proposed in the prior art to determine the lipid content in microalgae cells. Various examples of prior art techniques include gravimetric measurement of crude lipid extracts, fluorescence based partition assays, and gas chromatography.

Various conventional methods used for lipid determination require solvent extraction that requires separation of the solvent from crude extract after the extraction, which is followed by lipid quantification which may require fatty acid composition using chromatography techniques. Although these methods have been used widely and have a high accuracy in lipid detection, they are time and labour intensive, making it difficult to screen large numbers of algae. Thus, most conventional techniques for the determination of microalgae lipid content are time consuming and in most cases are indirect and require excessive sample preparations.

In essence, various prior art techniques are invasive, indirect, time intensive, and in some cases, experimentally unrepeatable. Moreover, some of the prior art techniques may be successfully applied only for certain microalgae. One such example is fluorescence based method. Several strains of microalgae with thick and rigid cell walls prevent penetration of the fluorescence dyes and therefore, render fluorescence based techniques unsuitable. In the event that such techniques may be applied, depending on the processing steps required, it typically takes from two hours to two days to determine the amount of lipid content. Evidently, the known characterisation techniques are inherently unsuitable for real-time monitoring. Therefore, it is not possible to realise an industrial automation system for controlling and adjusting the growth conditions in real-time to achieve a desired objective.

In light of foregoing, there is a need to develop new techniques for microalgal lipid characterisation to facilitate real-time monitoring, which could be integrated in-situ to adjust the growth conditions without the need for expensive and time consuming sample treatment and analysis techniques.

SUMMARY OF THE PRESENT INVENTION

It is therefore an object of the present invention to provide a method and a system that enable characterisation of amount of lipid content in a time efficient manner.

The object is achieved by a method and a system for lipid content characterisation according to claim 1 and claim 11 respectively. Further embodiments of the present invention are addressed in the dependent claims.

The underlying principle of the present invention is to exploit dielectric behaviour exhibited by microalgae when subjected to electromagnetic fields in a radio-frequency resonator resulting in a characteristic shift in frequency and magnitude of resonance.

The disclosed analytical techniques are based on Gaussian distribution modelling of a frequency response obtained from a resonator cavity provided with a microalgal suspension. When a resonator cavity is loaded with a microalgal suspension, the frequency response of the resonator cavity is altered based on intrinsic properties of the microalgal suspension. The intrinsic properties include, among others, the amount of lipid content in the microalgal suspension.

With various other factors such as the total suspension volume, the microalgal strain, and the cell concentration being maintained constant, a correlation is derived between shift in frequency and magnitude of resonance and the amount of lipid content. The frequency response obtained from a desired number of reference microalgal suspensions with known values of various process conditions including the amount of lipid content is measured to generate a set of reference parameters.

A set of sample parameters generated from a sample microalgal suspension using the same techniques is then correlated with the reference parameters. The amount of lipid content in the sample microalgal suspension is then determined on the basis of the reference microalgal suspension to which the reference parameters correspond. The amount of lipid content in the reference microalgal suspensions may be independently determined using any suitable microalgal lipid content characterisation technique.

In a first aspect of the present invention, a method for characterizing lipid content in microalgae is provided. At a first step, a sample microalgal suspension is provided in a resonator cavity. An input signal is then transmitted to the resonator cavity, wherein the input signal sweeps over a frequency range and a frequency response curve corresponding to the frequency range is determined based on an output signal reflected from the resonator cavity. Subsequently, a set of sample parameters is determined based on a Gaussian distribution modelling of the frequency response curve. Finally, an amount of lipid content in the sample microalgal suspension is determined based on correlation between the sample parameters and a set of reference parameters, wherein the reference parameters correspond to specific amounts of lipid content.

In a second aspect of the present invention, a system for characterizing lipid content in microalgae is provided. The system includes a resonator cavity, a vector network analyzer, and a computational module. The resonator cavity is configured for holding a sample microalgal suspension. The vector network analyzer is operationally coupled to the resonator cavity and configured for transmitting an input signal thereto. The input signal sweeps over a frequency range. The vector network analyzer is further configured for determining a frequency response curve corresponding to the frequency range based on an output signal reflected from the resonator cavity. The computational module is configured for determining a set of sample parameters based on a Gaussian distribution modelling of the frequency response curve, and determining an amount of lipid content in the sample microalgal suspension based on correlation between the sample parameters and a set of reference parameters, wherein the reference parameters correspond to specific amounts of lipid content.

Accordingly, the present invention provides a method and a system for characterisation of lipid content in a microalgal suspension through analysis of a frequency response of the microalgal suspension placed inside a resonator cavity. The techniques of the present invention advantageously provide rapid, reliable and sufficiently accurate lipid determination.

The data acquisition and data processing steps involved in determination of the amount of lipid content in a sample microalgal suspension according to the techniques of the present invention are highly time efficient and therefore, the time required for lipid content characterisation is significantly reduced.

The techniques of the present invention can therefore be implemented to realise an industrial automation system for controlling and adjusting the growth conditions based on real-time monitoring of the amount of lipid content in microalgae.

BRIEF DESCRIPTION OF THE DRAWINGS

The present invention is further described hereinafter with reference to illustrated embodiments shown in the accompanying drawings, in which:

FIGS. 2A-2C illustrate a bioreactor for cultivating microalgae, fluorescence microscopy images, and correlation chart between fluorescence intensity and amount of lipid content respectively in accordance with an embodiment of the present invention, FIG. 6 illustrates tuples of reference parameters along with corresponding amount of lipid content in accordance with an embodiment of the present invention.

DETAILED DESCRIPTION OF THE PRESENT INVENTION

Figure 1:
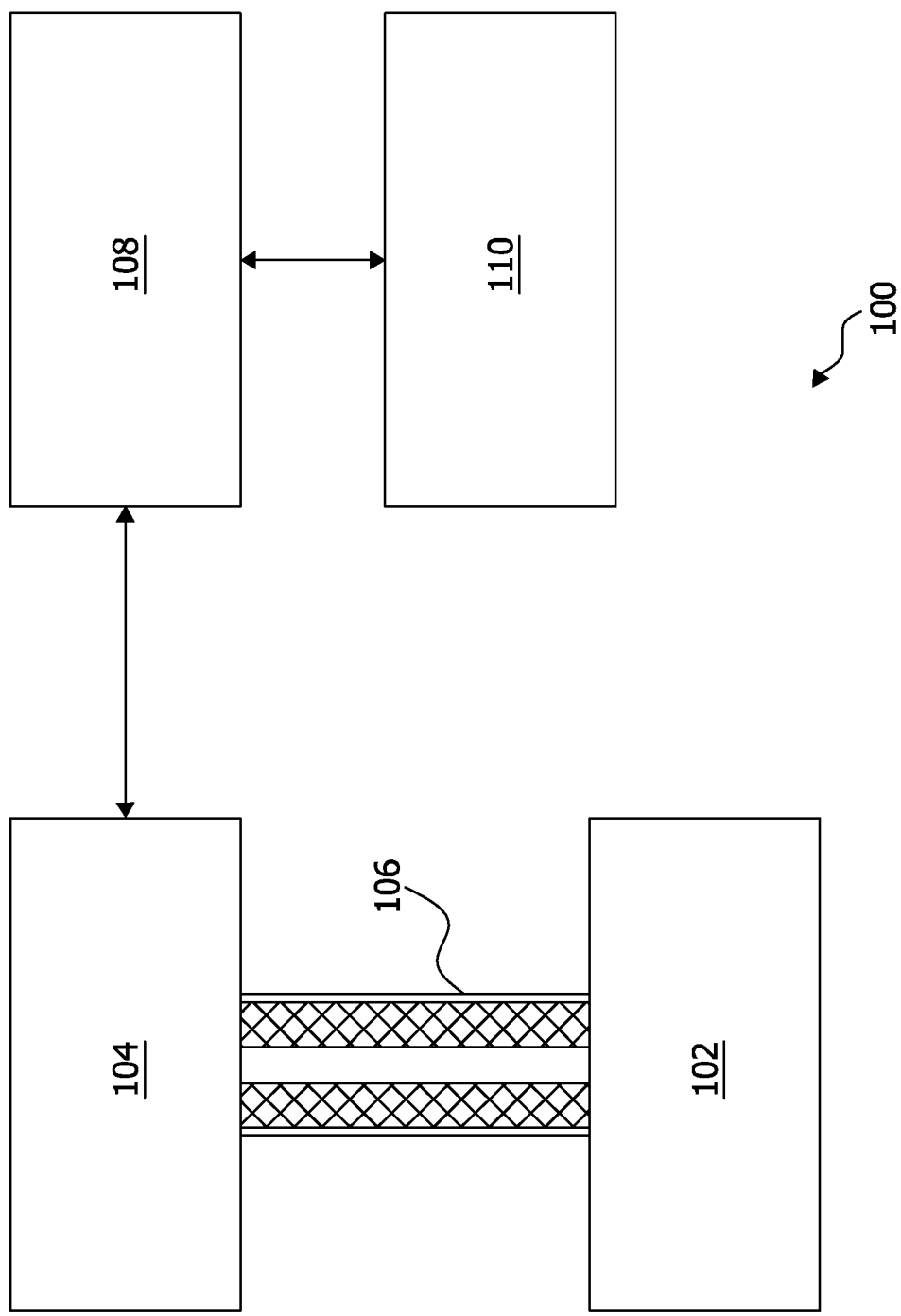
FIG. 1 illustrates a schematic view of a measurement system 100 for characterizing lipid content in microalgae in accordance with an embodiment of the present invention.

Various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details.

A radio-frequency resonator is formed using a transmission line bound by impendence discontinuities that cause reflection of radio-frequency waves. The radio-frequency resonators may be formed using specially configured cavities that are coupled with a radio-frequency signal source using any suitable means to provide radio-frequency excitation resulting in formation of electromagnetic fields within the cavity. A widely used simpler alternative is the open-ended resonator configuration. In such open-ended configuration, a transmission line is coupled to a radio-frequency source at one end while the other end is left open. The open end is then placed in vicinity or in direct contact with the material under test.

The techniques of the present invention will be generally explained in conjunction with an open-ended coaxial resonator structure as a non-limiting example. The teachings of the present invention may be implemented using any suitable radio-frequency resonator configuration.

In general, when a radio-frequency resonator interacts with a material under test, the radio-frequency response is altered based on dielectric properties of the material under test. The shift in radio-frequency response may then be used for various analytical purposes.

Referring now to FIG. 1, a schematic view of a measurement system 100 for characterizing lipid content in microalgae is illustrated in accordance with an embodiment of the present invention.

The measurement system 100 includes a resonator cavity 102, a vector network analyzer 104, a coaxial probe 106, a computational module 108, and a storage module 110.

The measurement system 100 is a radio-frequency based sensing system. It is generally known that radio-frequency or particularly microwave measurement cells can be used to characterise dielectric properties of materials.

The resonator cavity 102 is configured for holding a sample microalgal suspension. In the open-ended configuration, the resonator cavity 102 is simply a sample holder that is suitable for receiving and holding a sample microalgal suspension in vicinity of the open end of the coaxial probe 106.

The vector network analyzer 104 is operationally coupled to the resonator cavity 102 through the coaxial probe 106. The vector network analyzer 104 includes a radio-frequency signal generator that produces a radio-frequency signal that sweeps over a frequency range. The signal generator is coupled to the coaxial probe 106 through a directional coupler, a precision cable, and a connector port. The radio-frequency signal is transmitted as an input signal to the resonator cavity 102. The output signal reflected from the resonator cavity 102 is transmitted back to the vector network analyzer 104 through the coaxial probe 106. The directional coupler routes the output signal to a signal receiver. The signal receiver routes the output signal to a processing module which determines a frequency response curve corresponding to the frequency range of the input signal. In one exemplary embodiment, the frequency response curve is a scattering parameter curve corresponding to a reflection coefficient ($S_{11}$) of resonator cavity 102.

The computational module 108 is configured for determining a set of sample parameters based on a Gaussian distribution modelling of the frequency response curve. The storage module 110 stores a set of reference parameters. The set of reference parameters are previously retrieved using the same techniques from a set of reference microalgal suspensions with known amounts of lipid content. The reference parameters therefore correspond to specific amounts of lipid content. The computational module 108 correlates the sample parameters corresponding to the sample microalgal suspension with the reference parameters corresponding to the reference microalgal suspensions. The amount of lipid content in the sample microalgal suspension is determined on based on such correlation.

As indicated above, in one exemplary embodiment of the present invention, the frequency response curve corresponds to variation of a scattering parameter namely, the reflection coefficient ($S_{11}$). The variation of reflection coefficient may be analysed directly or indirectly, through tracking the return loss (RL) or voltage standing wave ratio (VSWR).

The frequency response curve is then subjected to Gaussian distribution modelling and the sample and reference parameters are extracted.

The sample parameters and the reference parameters using the above techniques correspond to magnitude, center frequency, bandwidth, and offset obtained from the output signal under test and calibration conditions respectively.

During the calibration stage, using the above techniques, the reference parameters are retrieved for the reference microalgal suspensions with the same microalgal strain and cell concentration as the sample microalgal suspension and also, known amounts of lipid content. The sample parameters are extracted for a sample microalgal suspension with known microalgal strain and cell concentration but unknown amount of lipid content.

Thus, the reference parameters are determined from a set of reference microalgal suspensions with predetermined microalgal strain, cultivation medium, and amount of lipid content. In accordance with techniques of the present invention, to achieve a more robust analytical system, the reference parameters for different microalgal strains with different cell concentrations and amounts of lipid content may be extracted and used for generating a reference library.

The storage module 110 is configured for storing the reference library of the reference parameters.

As will be further explained in conjunction with FIG. 6, the reference library comprises tuples of the reference parameters. Each tuple of the reference parameters corresponds to a specific amount of lipid content. The computational module 108 performs correlation between the sample parameters and the reference parameters on a tuple basis, and determines the amount of lipid content based on best match between tuples corresponding to the sample parameters and the reference parameters.

As will be further described in conjunction with FIG. 7, the reference library includes correlations between individual reference parameters and amount of lipid content. The computational module 108 performs correlation between the sample parameters and the reference parameters on an individual basis, and determines the amount of lipid content based on triangulation of a set of amounts of lipid content derived from individual reference parameters.

In accordance with an advantageous technique of the present invention, the reference library is indexed based on at least one or more of microalgal strains, cultivation media, and cell concentrations. Thus, when a sample microalgal suspension is to be analysed, the microalgal strain, cultivation medium, and cell concentration is specified and then, the computational module 108 then matches the sample parameters with the reference parameters indexed under the relevant category.

As will be evident from the above, the present invention includes two distinct phases, namely, a calibration phase and a test phase. Having briefly described the techniques of the present invention, the two phases will now be described in more detail.

Calibration Phase

Referring now to FIGS. 2A through 2C, a bioreactor 202 for cultivating microalgae, fluorescence microscopy images 204a through 204e, and correlation chart 206 showing between fluorescence intensity and amount of lipid content are respectively illustrated in accordance with an embodiment of the present invention.

The bioreactor 202 is used to cultivate microalgae of a given strain under laboratory environment.

In order to enhance lipid content in the microalgae a growth stress is applied and reference samples are collected over days of starvation. In one example, the growth stress is nitrogen deficiency which results in relatively higher levels of lipid accumulation in the microalgae. This is mainly attributable to the theory that protein synthesis is inhibited due to lack of nitrogen and therefore, excess carbon from photosynthesis is diverted into lipid production pathway.

The bioreactor 202 is used to obtain reference samples at regular intervals. The reference samples are subjected to sample preparation to obtain a desired concentration of the microalgal cells.

The reference samples are subjected to any suitable lipid content determination techniques such as fluorescence, gravimetric, chromatographic and so on. In one example, fluorescence technique is used. FIG. 2B shows fluorescence microscopy images 204 of microalgal cells over progressive days of nitrogen starvation. The correlation chart 206 shows amount of lipid content (as a percentage of dry mass) in the reference microalgal suspensions. In the adjoining figure, (○) represent lipid content while (•) represent relative fluorescent intensity.

The amount of lipid content in each reference microalgal suspension thus obtained is recorded and stored.

Certain general principles related to the techniques of the present invention will now be explained in conjunction with FIGS. 3A through 3C and FIGS. 4A through 4C.

Figures 3A, 3B, 3C:
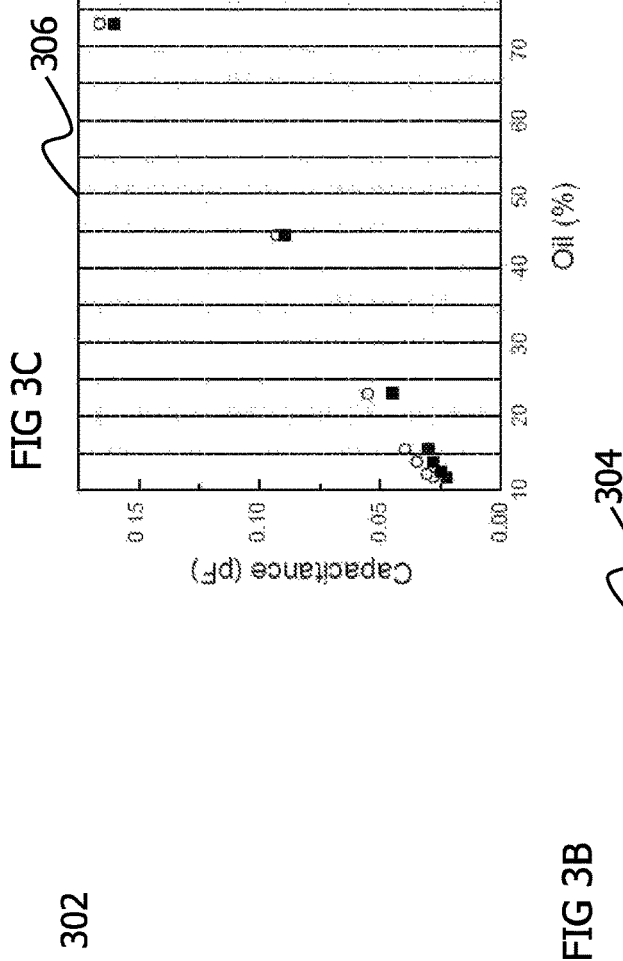
FIGS. 3A-3C illustrate an optical image of a microalgae, schematic representation of polarisation of microalgae under the influence of an electromagnetic field, and impedance characteristics chart showing variation of resistance and capacitance under varying amounts of lipid content in microalgae in accordance with an embodiment of the present invention.

Referring now to FIGS. 3A through 3C, an optical image of a microalgae 302, a schematic representation 304 of polarisation of microalgae under the influence of an electromagnetic field, and impedance characteristics chart 306 showing variation of resistance and capacitance under varying amounts of lipid content in microalgae are illustrated in accordance with an embodiment of the present invention.

The size of microalgae, especially those used for biofuel, is typically in the range of few micrometers. Thus, when subjected to electromagnetic fields, microalgae is susceptible to polarisation owing to induced charging effects. FIG. 3A shows a microscopic image 302 of *Scenedesmus* sp., which is approximately in the range of several of micrometers while FIG. 3B shows induced charges that develop when microalgal cells are subjected to a radio-frequency field.

It will therefore be appreciated that microalgae can be modelled as an electrical dipole, which has two pair of electrical charges of equal magnitude but opposite sign, separated by some distance.

Thus, a microalgal suspension affects the field distribution inside a resonator cavity and consequently, input impedance and resonance frequencies are changed, which in turn, are reflected in the frequency response of the resonator cavity.

The extent of propagation of radio-frequency fields through microalgal cells is affected by the intrinsic physical properties of the microalgae, namely its dielectric constant and electrical resistive losses. Therefore, the radio-frequency fields propagated through microalgal suspension are altered in magnitude and phase depending on the type, composition, and concentration of microalgal cells in the suspension.

The techniques of the present invention are developed based on dielectric behaviour resultant from intrinsic material properties of microalgal cells and correlation between shift in radio-frequency response and such intrinsic material properties.

According to the teachings of the present disclosure, when other factors such as microalgal strain, cell concentration, and cultivation medium are maintained constant, the frequency response of a resonator cavity directly correlates to the amount of lipid content in microalgal cells.

Referring particularly to FIG. 3C, impedance characteristics chart 306 between capacitance and resistance values and amount of lipid content in a microalgal suspension is depicted. In the adjoining figure, (○) represent resistance while (•) represent relative capacitance.

In one exemplary embodiment of the present invention, an open-ended coaxial resonator is used. The radio-frequency propagation is confined and guided inside the coaxial cable. The open-end of this cable forms a capacitance within which a microalgal suspension acts as a dielectric material. The initial capacitance corresponds to lipid free content and exhibits low value with low resistive losses and high quality factor. As the lipid content increases, the effective dielectric constant of the solution increases. The equivalent capacitance and resistance values corresponding to varying amounts of lipid contents in the reference microalgal suspensions are depicted in the adjoining figure, FIG. 3C. As can be seen, both capacitance and resistance show a linear relationship with the amount of lipid content.

Figure 4C:
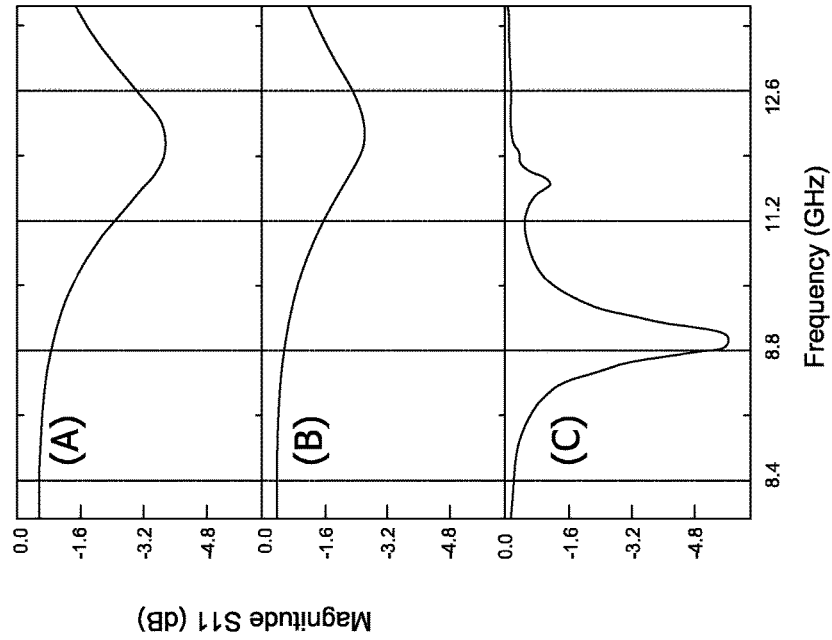
FIGS. 4A-4C illustrate curves for scattering parameter at varying amounts of lipid content, resonance frequency at varying cell concentrations, and scattering parameters at varying microalgal strains respectively in accordance with an embodiment of the present invention.
Figure 4A:
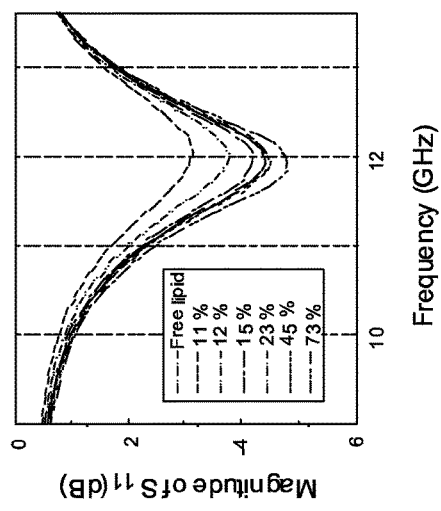
Figure 4B:
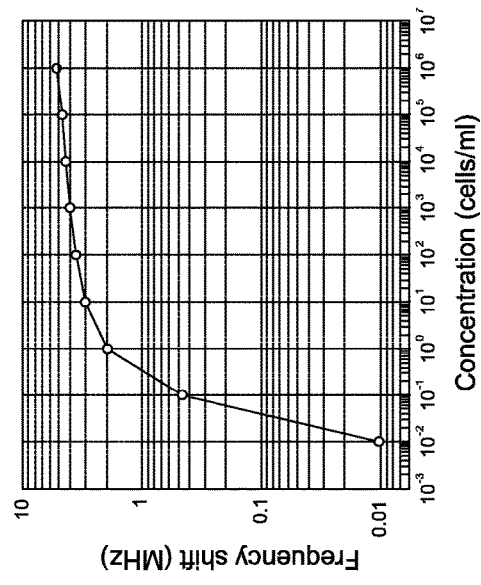

Referring now to FIGS. 4A through 4C, curves for scattering parameter at varying amounts of lipid content, resonance frequency at varying cell concentrations, and scattering parameters at varying microalgal strains are respectively illustrated in accordance with an embodiment of the present invention.

The change in magnitude level of scattering parameter ($S_{11}$) is associated with change in the electrical direct current resistance of a microalgal suspension. On the other hand, the frequency shift is associated with the change in capacitance.

Owing to the dielectric behaviour of microalgal suspensions, a shift in resonance frequency and a gradual increase in resonance magnitude occur in an open-ended coaxial resonator as the amount of lipid content in the microalgal cells increases. The shift in response parameters is calibrated against the amount of lipid content and is then subsequently used for rapid characterisation of lipid content in a sample microalgal suspension.

With other factors being constant, the change is frequency response curve derived based on the reflection coefficient ($S_{11}$) is depicted in FIG. 4A.

In general, it is recognised that selectivity and sensitivity are two important attributes that should be addressed in any characterisation technique.

The sensitivity of the techniques of the present disclosure is evident from FIG. 4B. The figure depicts frequency shift obtained by diluting a known concentration of a microalgal cells with cultivation medium solution. As will be evident, the disclosed technique is sufficiently sensitive to allow determination of lipid content generated during early-stage cell growth. The figure shows that the frequency shift decreases as microalgal cell concentration decreases. The radio-frequency screening advantageously has higher sensitivity than various other conventional methods, and thus allows better limit of detection without the need of any treatment or labeling.

The selectivity of the disclosed techniques is evident from FIG. 4C, which depicts the frequency response curves corresponding to different microalgal strains with identical concentration. Thus, each microalgal strain is associated with a certain shift in resonance frequency and magnitude and in effect, can be assigned a unique radio-frequency signature. Specifically, the adjoining figure specifically shows radio-frequency responses (A) and (B) and for two different types of microalgae (*Scenedesmus* sp. And *Nannochlorpsis* sp.). The third radio-frequency response (C) corresponds to extracted lipid contents as a reference. The two strains used are different in size, composition, and thus, different dielectric constants and resistive losses, and accordingly, different resonance frequencies, which in turn result in different radio-frequency responses. Thus, the techniques of the present invention can be used for not only determining the lipid content of other strains, but also identifying the microalgal strain.

Having now explained key underlying technical principles of the present invention, further details of the calibration phase will now be explained.

Figure 5B:
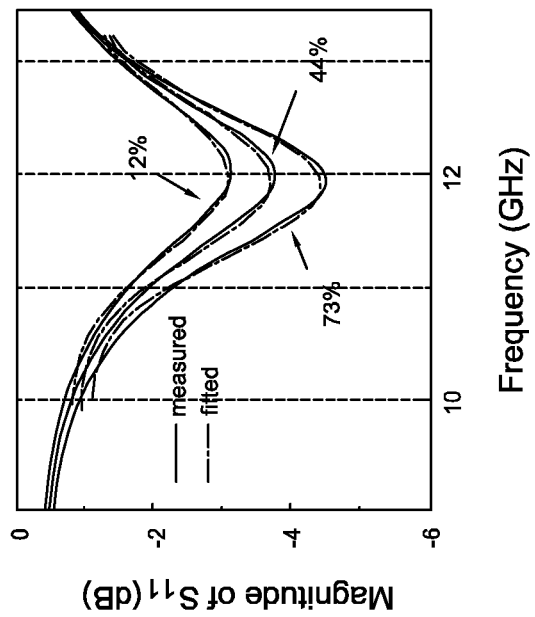
FIGS. 5A-5B illustrate curves for scattering parameter at varying amounts of lipid content and superimposed Gaussian distribution models respectively in accordance with an embodiment of the present invention.
Figure 5A:
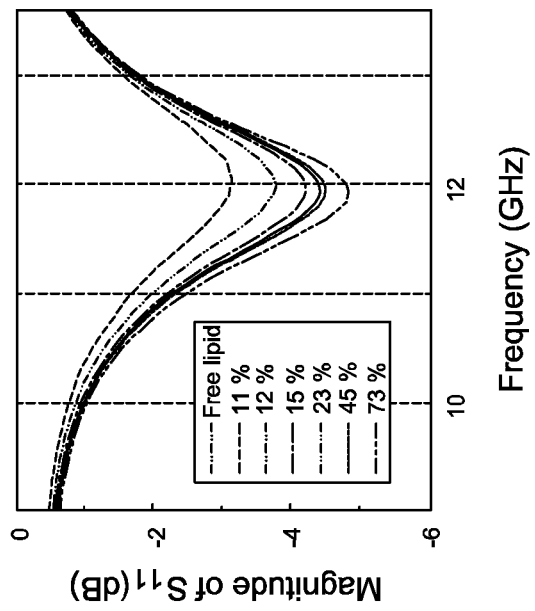
Figure 7B:
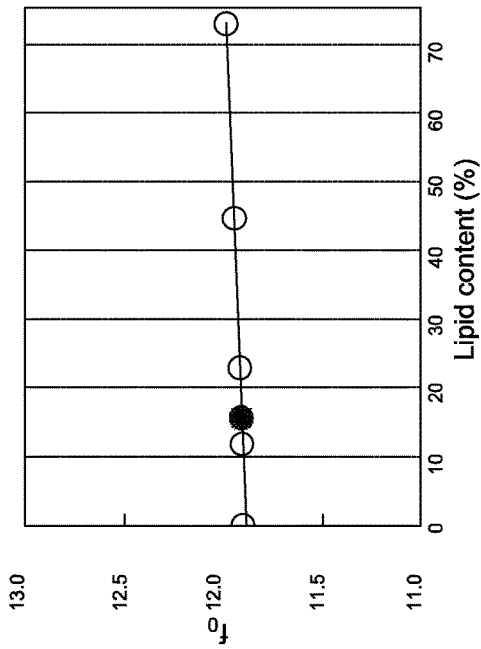
FIGS. 7A-7D illustrate correlation between magnitude, center frequency, bandwidth, and offset and amount of lipid content in microalgae in accordance with an embodiment of the present invention.
Figure 7D:
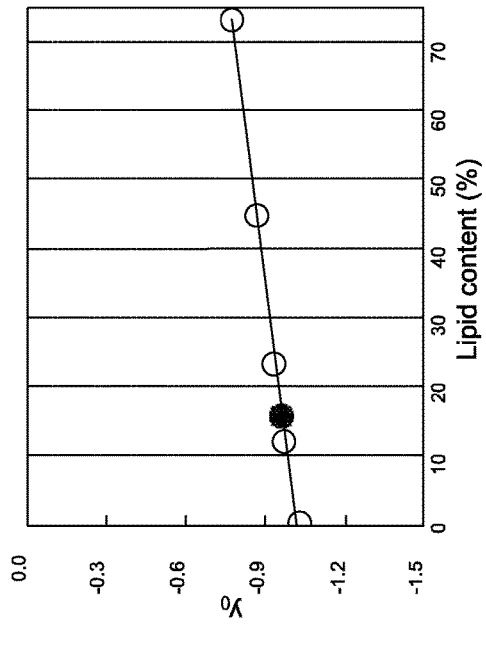
Figure 7A:
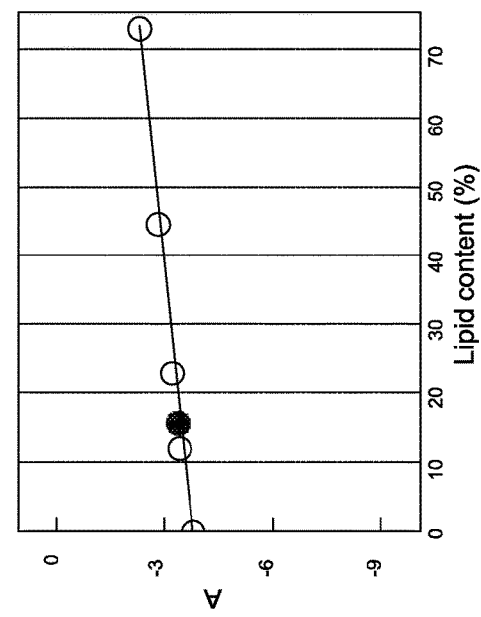
Figure 7C:
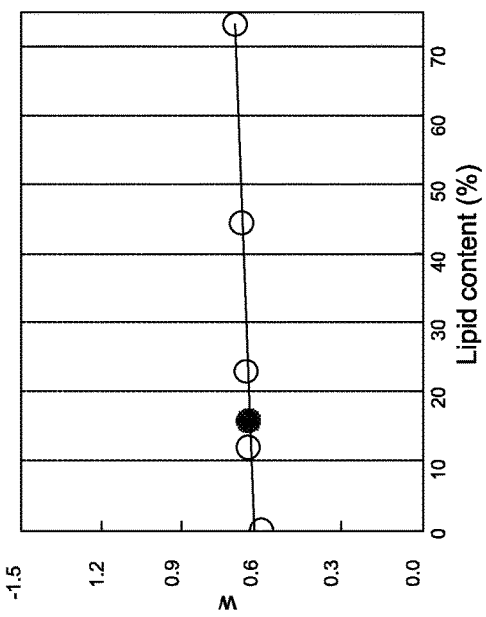

Referring to FIGS. 5A and 5B, curves for scattering parameter at varying amounts of lipid content and superimposed Gaussian distribution models are respectively illustrated in accordance with an embodiment of the present invention.

The reference microalgal suspensions are obtained as explained in conjunction with FIG. 2 and subjected to lipid content determination using any suitable analytical techniques known in the art.

The scattering parameter curves at varying amounts of lipid content shown in FIG. 5A are same as those shown in FIG. 4A and are reproduced here for ease of reference.

It should be noted that careful calibration of vector network analyzer 104 is required to ensure that the frequency response curve obtained from a reference sample in fact corresponds to the amount of lipid content in the reference microalgal suspension. To achieve this, the calibration is performed to ensure that the measurement reference plane is shifted to the end of the coaxial probe 106.

Subsequent to determination of the scattering parameter curve, a Gaussian distribution model is created as per the following equation:

$$G(f) = y_0 + Ae^{-0.5\left(\frac{f-f_0}{w}\right)^2} \tag{1}$$

where, $y_0$, $A$, $f$, $f_0$, and $w$ are offset, magnitude, frequency, center frequency and bandwidth of the resonance respectively.

As can be seen in the adjoining figures, particularly in FIG. 5B, the Gaussian distribution model provides a good approximation of the frequency response curve and thereby, facilitates determination of offset, magnitude, frequency, center frequency and bandwidth associated with the resonator cavity 102 loaded with the microalgae suspension.

These parameters derived from each reference microalgal suspension are stored as reference parameters along with corresponding amount of lipid content of the reference microalgal suspension.

Similar measurement and analysis is conducted for multiple reference microalgal suspensions to create a reference library. The reference library may store the reference parameters in various different manners. FIG. 6 and FIG. 7 show two different embodiments in which this information may be organised.

FIG. 6 illustrates tuples of reference parameters along with corresponding amount of lipid content and FIGS. 7A-7D illustrate correlation between magnitude, center frequency, bandwidth, and offset and amount of lipid content in microalgae in accordance with an embodiment of the present invention.

In the embodiment shown in FIG. 6, the information is stored in the form of tuples. The reference library is stored in the storage module 110.

In an alternative embodiment of the present invention, the correlations between individual reference parameters and amount of lipid content is derived, as shown in FIG. 7. The reference library, in this embodiment, includes this correlation. As will be appreciated, while only a finite number of reference microalgal suspensions may be analysed during calibration phase, the resulting correlation between individual reference parameters and amounts of the lipid content extrapolates the correlation over broader range of values of the reference parameters and amounts of lipid content.

In various embodiments of the present invention, a significantly larger number of reference microalgal suspensions with different microalgal strains, cultivation medium, cell concentrations, and amount of lipid content may be analysed during the calibration phase to create a robust reference library. In accordance with an advantageous feature of the present invention, the reference library is indexed based on at least one or more of microalgal strains, cultivation media, and cell concentrations to enable more rapid analysis during the test phase.

Test Phase

During the test phase, a sample microalgal suspension is obtained. Preferably, the microalgal strain and the cultivation medium are known. Additionally, the cell concentration is either known or determined. If desired, the sample is treated to obtain a desired cell concentration.

Subsequently, with the vector network analyzer 104 suitably calibrated, the frequency response curve is obtained and sample parameters are obtained in a manner similar to that used for obtaining reference parameters during the calibration phase.

Thereafter, the sample parameters are correlated with the reference parameters to determine the amount of lipid content in the sample microalgal suspension.

To achieve this, two alternative correlation techniques may be followed. In a first example, correlation between the sample parameters and the reference parameters is performed on a tuple basis. The amount of lipid content is determined based on the best match between tuples corresponding to the sample parameters and the reference parameters. In case an exact match is not available, any suitable mathematical techniques may be used to find the best match or derive the amount of lipid content based on extrapolation of amounts of lipid content corresponding to a set of matching tuples. In one embodiment, tuple-wise distances are measured and two closest tuples are selected and the amount of lipid content in the sample microalgal suspension is then determined to be a weighted average of the amounts of lipid content in the two reference microalgal suspensions based on relative distances between the sample parameters tuple and the reference parameters tuples.

In an alternative example, correlation between the sample parameters and the reference parameters is done on an individual basis using the extrapolated correlation curves shown in FIG. 7. In the event that the individual parameter-wise comparison yields different amounts of lipid content in the sample microalgal suspension, the amount of lipid content is determined based on triangulation of a set of amounts of lipid content derived from individual reference parameters using any suitable mathematical technique, such as weighted average of amounts of lipid content obtained from the parameter-wise comparisons.

Figure 8:
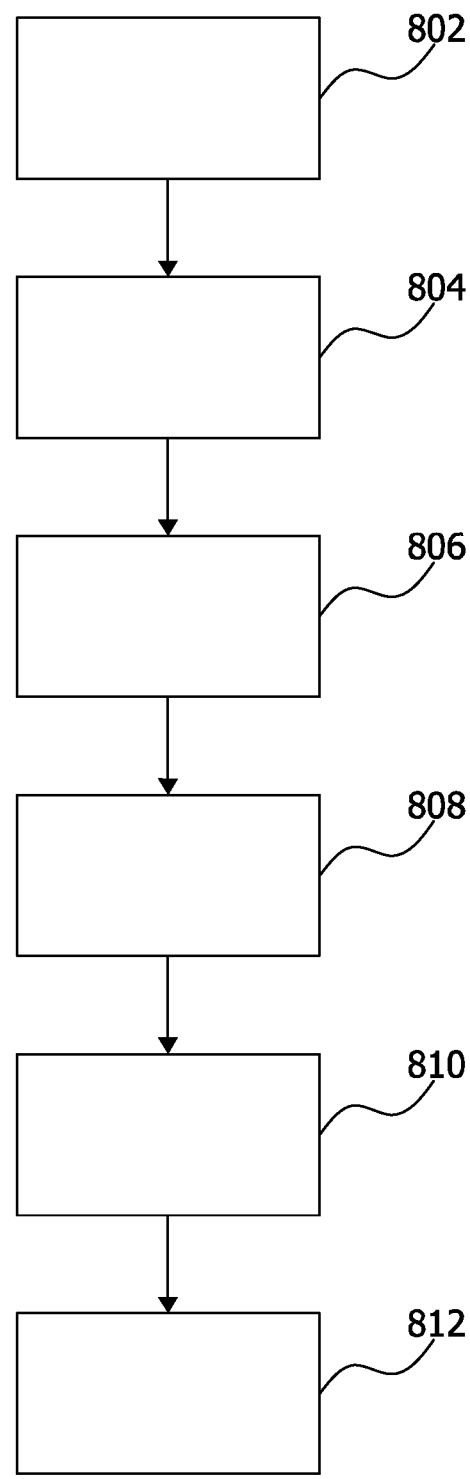
FIG. 8 illustrates a method for characterizing lipid content in microalgae in accordance with an embodiment of the present invention.

Referring now to FIG. 8, a method for characterizing lipid content in microalgae is illustrated in accordance with an embodiment of the present invention.

Prior to performing the steps for characterising the amount of lipid content in microalgae, it is required to generate a reference library of reference parameters. In the adjoining figure, the reference library is generated at step 802.

The reference library includes tuples of the reference parameters and wherein each tuple corresponds to a specific amount of lipid content. Alternatively or additionally, the reference library includes correlations between individual reference parameters and amount of lipid content. In one embodiment, the reference library is indexed based on at least one or more of microalgal strains, cultivation media, and cell concentrations.

At step 804, a sample microalgal suspension is provided in a resonator cavity.

Subsequently, at step 806, an input signal is transmitted to the resonator cavity, wherein the input signal sweeps over a frequency range and at step 808, a frequency response curve corresponding to the frequency range is determined based on an output signal reflected from the resonator cavity. In one embodiment, the frequency response curve corresponds to variation of a scattering parameter ($S_{11}$).

At step 810, a set of sample parameters is determined based on a Gaussian distribution modelling of the frequency response curve.

Finally, at step 812, an amount of lipid content in the sample microalgal suspension is determined based on correlation between the sample parameters and a set of reference parameters, wherein the reference parameters correspond to specific amounts of lipid content.

In various exemplary embodiments of the present invention, the sample parameters and the reference parameters correspond to magnitude, center frequency, bandwidth, and offset obtained from the output signal reflected from the resonator cavity under test and calibration conditions respectively.

The reference parameters are determined from a set of reference microalgal suspensions with predetermined microalgal strain, cultivation medium, and amount of lipid content.

In one exemplary embodiment, the correlation between the sample parameters and the reference parameters is performed on a tuple basis, and the amount of lipid content is determined based on best match between tuples corresponding to the sample parameters and the reference parameters.

In an alternative embodiment, the correlation between the sample parameters and the reference parameters is performed on an individual basis, and the amount of lipid content is determined based on triangulation of a set of amounts of lipid content derived from individual reference parameters.

EXPERIMENTAL DATA

The experimental data provided herein below is obtained using these techniques and underlying principles of the present invention described above.

As will be understood from the description provided above, the techniques of the present invention are based on measuring high frequency scattering parameters ($S_{11}$) of microalgae suspensions placed in an open-ended coaxial RF resonator structure. The experimental results are provided below.

Although the experimental results obtained using a specific microalgal strain are being provided herein below, it should be noted that it is not intended to limit the scope of the present invention in any manner whatsoever. The techniques of the present invention are applicable to determination of amount of lipid content in any strain of microalgal population.

Strain and Culture Medium

*Scenedesmus* sp. culture was obtained from Algal Oil Company, Philippines, and cultivated in a nitrogen deficient modified Bassel medium (—N-BBM), which is composed of (in mM); 0.17 $CaCl_2.2H_2O$, 0.3 $MgSO_4.7H_2O$, 1.29 $KH_2PO_4$, 0.43 $K_2HPO_4$, 0.43 NaCl, 1 ml·$L^{-1}$ of Vitamine $B_{12}$, and 6 ml·$L^{-1}$ of P-IV solution that consisted of 2 $Na_2EDTA.2H_2O$, 0.36 $FeCl_3.6H_2O$, 0.21 $MnCl_2.4H_2O$, 0.37 $ZnCl_2$, 0.0084 $CoCl_2.6H_2O$ and 0.017 $Na_2MoO_4.2H_2O$.

Other Materials n-Hexane, acetone, Nile Red (9-diethylamino-5-benzo[α] phenoxazinone), dimethyl sulfoxide (DMSO), were used to perform various analytical techniques.

Sample Preparation

The microalgae was grown in a nitrogen deficient medium (—N-BBM) for three weeks, to enhance the biomass productivity, in a 5 L bubble column photo-bioreactor with an internal illumination (FIG. 2A). All cultivations in this work were autotrophic, with $CO_2$ naturally present in air bubbled through the suspension being the sole carbon source.

Prepared medium was sterilized in an autoclave (Hirayama HV-50, Japan) at 121 degree Centigrade for 15 min and cooled to room temperature prior to use. The photo-bioreactor was illuminated with one 50 cm, 60 watts, white fluorescent light at a light intensity of 120 μmol·$m^{-2}$·$s^{-1}$, measured using a light meter under 12 h light/dark photoperiod automatically controlled by a 24 hrs timer (S2402, China). The photo-bioreactor had an outer diameter of 10 cm, an inner diameter of 5 cm and a height of 40 cm.

The cell growth was monitored daily by measuring the optical density at 680 nm using a spectrophotometer (Shimadzu UV-1800 UV, Kyoto, Japan). The samples were measured twice and the average values were considered. The cells concentration (cells·$ml^{-1}$) at any given cultivation time was calculated from a pre-prepared calibration curve of the optical density at 680 nm versus cells concentration determined using Neubauer Hemocytometer, placed on a microscope (Eclipse LV100 Pol, Nikon, Japan). The dry weight of algal biomass was also determined by filtering the algal suspension using a Whatman filter paper, dried overnight at 105 degree Centigrade in an oven (Memmert, Germany) until constant weight.

The process of developing a correlation for lipid content as function of scattering parameter $S_{11}$ for a specific kind of microalgae, with predetermined cells concentration, starts with taking a sample from a bioreactor, diluting it to a constant cells concentration and then placing it in a RF resonator structure.

Samples were collected at regular intervals and diluted in growth medium to obtain a 4 ml of cell suspension. FIG. 2A shows the bioreactor from which the samples were collected over days of starvation. The primary stress applied was nitrogen deficiency, where accumulations of more than 70% (dry basis) have been achieved. This is mainly due to the lack of nitrogen required for protein synthesis, and the excess carbon from photosynthesis is then diverted into lipid production pathway. The Nile Red stock solution was used for performing fluorescence-based analysis. FIG. 2B shows the fluorescence microscopy images of cells stained with Nile Red that shows the lipid accumulation with days of nitrogen starvation. FIG. 2C shows a comparison between the actual lipid content and the fluorescence intensity determined by the plate reader.

Cells concentration was determined by the cell counting technique, where 0.1 mm deep hemocytometer (PZO, Poland). Different culture dilutions were prepared to calibrate cells concentration versus adsorption using UV spectrophotometer (Hach DR-5000, Germany) at 680 nm. Two ml of the well mixed culture are withdrawn from the flask and diluted to 4 ml in growth medium. This dilution step was repeated four times. 0.1 ml droplet of 1:16 diluted were placed on a slide of 0.0025 $m^2$, using Pasteur pipette, and covered with 22×22 mm square cover slip. Cells were allowed to settle for 2 min and then the number of cells was counted in the four squares at the corner of the hemocytometer grid of nine large squares of 1 $mm^2$ surface area. Total cells concentration per ml was calculated using Eq (2), from which the initial concentration was determined by multiplying the concentration by 16.

$$\text{Cells concentration} = \frac{\text{Total counted cells}}{4} \times 10^4$$

A calibration curve between cell count and the spectrophotometer absorption reading was generated and used in subsequent analysis to convert the spectrophotometer readings into cells concentration. The cells counting and dry weight analysis are standard procedures to determine cells and biomass consecrations. Further details of the procedure can be found in the state of the art.

Calibration Phase Determination of Lipid Content

Samples were collected at regular intervals and diluted in growth medium to obtain a 4 ml of cell suspension. The accumulations were monitored by staining the constant concentration samples (1.5×$10^6$ cells·$ml^{-1}$). With Nile Red that emits a yellow fluorescent signal in the presence of the lipid, the fluorescents were visualized using fluorescence microscope (Olympus).

The Nile Red stock solution was prepared by dissolving 0.1 mg of Nile Red in 1 ml acetone, and the solution was stored in the dark at 4° C.

Culture samples (500 μl) were placed in an eppendorf tube, span in a centrifuge (Sigma 113, Germany) for 30 s at 4,000 rpm and 410 μl of the supernatant were taken. DMSO (10 µl) was then added to promote the accessibility of Nile Red into the cells. The culture was then vortexed and 1 µl of Nile Red solution was added followed by 20 min incubation in the dark. The lipid accumulations were then quantified using Multi-label Plate Reader (Perkin-Elmer, Boston) with black 96-well plates. The cells were harvested by centrifugation and then lyophilized in a freeze drier (Telstar, Terrassa, Spain) operated at −54° C. and 0.02 mbar for 6 hrs.

The actual lipid contents of the microalgae were determined using Soxhlet extraction technique with n-hexane and subsequently calibrated against their respective radio frequency signature at a later stage. The n-hexane can extract the non-polar lipids only, which are the interesting lipids for biodiesel production. Hence, the measurements were limited to them only, and *Scenedesmus* sp. microalgae lipid composition was calculated as tabulated below.

| Fatty acid methyl ester | % Composition |
| --- | --- |
| Methyl myristate | 12.5 |
| Methyl sterate | 6.3 |
| Cis-9-oleic Methyl ester | 12.5 |
| Trans-9-elaidic Methyl ester | 43.8 |
| Methyl linoleate | 18.8 |
| Methyl behanate | 6.3 |

Radio Frequency Response Curve

A network analyzer is used to measure the scattering parameter of the suspended material which is recorded and then processed to extract the change in frequency and magnitude.

The network analyzer (NA) from Rohde and Schwartz (R&S®ZVL) is commonly used to measure S-parameters, because reflection and transmission of electrical networks are easily measured at high frequencies. The vector network analyzer includes radio frequency generators that produce power signals at different frequencies, thus when these power signals propagate inside the cultivation medium they scatter back towards the source and some portion of this signal power is absorbed by the microalgae particles.

The system was calibrated using the SLOT transmission line techniques for the network analyzer. A typical calibration moves the measurement reference planes to the end of the test cables. Therefore, it excludes the effect of losses and phase shifts that could add noise to the measured signal. Each microalgae suspension, of different lipid content, was exposed to a radio frequency signal with a power of 10 dBm and with a sweep from 8 GHz up to 13.6 GHz (the equipment measurements range capability). The self-resonance frequency of the coaxial cables was ensured to be pushed above 30 GHz; so it does not affect the measurements in the mentioned range.

In order to confirm the concept, a sample of *Scenedesmus* sp. microalgal suspension was withdrawn from the bioreactor and concentrated at fixed cells concentration of $1.5 \times 10^6$ cells/ml, and then inserted inside the open-ended coaxial resonator as indicated in FIG. 1. The setup was calibrated before each measurement has been carried out. This calibration ensured that the measurement actually represented the sample under test while excluding the effect of losses and phase shifts due to the cables and host structure which could add noise to the measured signal. A blank was prepared by harvesting the microalgae cells and its lipid content was completely extracted, and then rediluted in growth medium in the same concentration of $1.5 \times 10^6$ cells/ml.

The set of $S_{11}$ parameter measured curves versus frequency for different lipid contents are shown in FIGS. 4A and 5A. The RF response of the suspended microalgae indicates the lipid accumulations as the magnitude of the $S_{11}$ changes gradually with the increase in lipid content. The $S_{11}$ curve shows a smooth performance over frequency and exhibits resonance with specific resonance frequency, bandwidth and magnitude. All of these parameters vary with the lipid content. The resonance frequency of samples free of lipids (i.e., all lipids have been extracted) was found to be higher than that of samples of higher lipid content, due to the change in the effective suspended solution dielectric constant.

Determination of Characteristic Parameters

The lipid content was calibrated against the change in resonance parameters. The resonance can be predicted with the Gaussian distribution function. Gaussian function parameters were correlated with the RF measured parameters, namely, its bandwidth, magnitude and center frequency. A general Gaussian function could be expressed by Equation (1) mentioned earlier and reproduced below:

$$G(f) = y_0 + Ae^{-0.5\left(\frac{f-f_0}{w}\right)^2} \quad (1)$$

where, $y_0$, A, f, $f_0$, and w are offset, magnitude, frequency, center frequency and bandwidth of the resonance respectively. These set of parameters were correlated against lipid content.

The predicted and measured $S_{11}$ response corresponding to lipid contents of 12.10, 44.5 and 73.2% were drawn against each other as shown in FIG. 5B. The prediction was carried out from 10 GHz to 13.5 GHz, the resonance window. FIG. 5B reveals a good agreement between the predictions and measurements, with a standard deviation of ±0.001. The set of parameters {$y_0$, A, $f_0$, and w} were determined for different lipid contents by fitting each measured curve in FIG. 5A with Equation (1). The predicted coefficients are presented in FIG. 6, with each row represents specific lipid content.

The analysis of resonance parameters over lipid content variation, as depicted in FIG. 7, showed that the predicted set of parameters versus lipid content exhibited a linear relationship. As the lipid content increased, the offset and magnitude parameters changed in the same manner, while both center frequency and bandwidth exhibited identical behaviour.

Test Phase Determination of Lipid Content

The model was validated by measuring radio frequency response of a sample of unknown lipid content. The measured radio frequency signal was fitted to Equation (1) and the associated coefficients were determined and located on the calibration curves shown in FIG. 7. The lipid content that correspond to these values was then determined to be 12.05%. The actual lipid content of the sample was measured using the conventional Soxhelt technique and found to be of 12.08%, which is almost identical to that predicted by the model with an error of only 0.2%. This clearly proved that the proposed technique predicts the amount of lipid content with sufficient accuracy.

The accuracy of the proposed model is approximately 98%, and the recorded error associated with the lower and higher contents did not exceed 2% in the entire range of measured lipid content. The error can be further optimized by involving more measured points and by having micro cavity resonator dedicated design. The calibration curve thus can be used to determine the amount of lipid content of an unknown sample from measuring the $S_{11}$ frequency response and Gaussian prediction.

The experimental data provided above uses radio frequency based analysis for lipid content determination. The conducted measurements and determined calibration model are in respect of the specific microalgae strain, grown in the specific cultivation medium under certain set of conditions mentioned in this work. If the same strain used is grown in the same medium, under same conditions, then the effects of any possible relative variations are eliminated. The same method can be applied to other strains, grown in other media/conditions.

The present invention provides new techniques that utilize radio frequency for rapid lipid quantification without the need for sample preparation. The average duration of lipid quantification using the proposed technique was of about one minute, which is significantly less than all other conventional techniques, and was achieved without the need for any time consuming treatment steps.

Thus, the present invention provides a technique for rapid measurement of the amount of lipid content in a microalgal suspension. Owing to fast detection, the present invention enables controlling and rapidly adjusting the growth conditions for cultivating microalgae to achieve a desired objective.

The proposed method provided a better combination of high sensitivity, fast response of less than one minute, low cost, high throughput, and ease of use. When compared with other lipid determination techniques, the developed approach is much time and cost efficient. The repeatability studies demonstrate good accuracy.

The technique of the present invention can be applied to in-situ measurements, which will pave the way for direct and rapid determination of microalgae lipid content and also enable optimization and selection of species and growth conditions.

Although the present disclosure specifically focuses on lipid content determination in microalgae, the teachings can generally be applied to any other biological entities of interest.

While the present invention has been described in detail with reference to certain embodiments, it should be appreciated that the present invention is not limited to those embodiments. In view of the present disclosure, many modifications and variations would present themselves, to those of skill in the art without departing from the scope of various embodiments of the present invention, as described herein. The scope of the present invention is, therefore, indicated by the following claims rather than by the foregoing description. All changes, modifications, and variations coming within the meaning and range of equivalency of the claims are to be considered within their scope.

What is claimed is:

1. A method for characterizing lipid content in microalgae, said method comprising:
    providing a sample microalgal suspension in a resonator cavity;
    transmitting an input signal to said resonator cavity, wherein said input signal sweeps over a frequency range;
    determining a frequency response curve corresponding to said frequency range based on an output signal reflected from said resonator cavity;
    determining a set of sample parameters based on a Gaussian distribution modelling of said frequency response curve; and
    determining an amount of lipid content in said sample microalgal suspension based on correlation between said sample parameters and a set of reference parameters, wherein said reference parameters correspond to specific amounts of lipid content.

2. The method according to claim 1, wherein said frequency response curve corresponds to variation of a scattering parameter.

3. The method according to claim 1, wherein said sample parameters and said reference parameters correspond to magnitude, center frequency, bandwidth, and offset obtained from said output signal reflected from said resonator cavity under test and calibration conditions respectively.

4. The method according to claim 1, wherein said reference parameters are determined from a set of reference microalgal suspensions with predetermined microalgal strain, cultivation medium, and amount of lipid content.

5. The method according to claim 1 further comprising generating a reference library of said reference parameters.

6. The method according to claim 5, wherein said reference library comprises tuples of said reference parameters and wherein each tuple corresponds to a specific amount of lipid content.

7. The method according to claim 6, wherein correlation between said sample parameters and said reference parameters is performed on a tuple basis, and said amount of lipid content is determined based on best match between tuples corresponding to said sample parameters and said reference parameters.

8. The method according to claim 5, wherein said reference library comprises correlations between individual reference parameters and amount of lipid content.

9. The method according to claim 8, wherein correlation between said sample parameters and said reference parameters is performed on an individual basis, and said amount of lipid content is determined based on triangulation of a set of amounts of lipid content derived from individual reference parameters.

10. The method according to claim 5, wherein said reference library is indexed based on at least one or more of microalgal strains, cultivation media, and cell concentrations.

11. A system for characterizing lipid content in microalgae, said system comprising:
    a resonator cavity, said resonator cavity configured for holding a sample microalgal suspension;
    a vector network analyzer, said vector network analyzer operationally coupled to said resonator cavity for transmitting an input signal thereto, wherein said input signal sweeps over a frequency range, and further configured for determining, using a processing module, a frequency response curve corresponding to said frequency range based on an output signal reflected from said resonator cavity; and
    a computational module accessible by the processing module, said computational module configured for determining a set of sample parameters based on a Gaussian distribution modelling of said frequency response curve, and determining an amount of lipid content in said sample microalgal suspension based on correlation between said sample parameters and a set of reference parameters, wherein said reference parameters correspond to specific amounts of lipid content.

12. The system according to claim 11, wherein said frequency response curve corresponds to variation of a scattering parameter.

13. The system according to claim 11, wherein said sample parameters and said reference parameters correspond to magnitude, center frequency, bandwidth, and offset obtained from said output signal under test and calibration conditions respectively.

14. The system according to claim 11, wherein said reference parameters are determined from a set of reference microalgal suspensions with predetermined microalgal strain, cultivation medium, and amount of lipid content.

15. The system according to claim 11 further comprising a storage module accessible by the processing module and configured for storing a reference library of said reference parameters.

16. The system according to claim 15, wherein said reference library comprises tuples of said reference parameters and wherein each tuple corresponds to a specific amount of lipid content.

17. The system according to claim 16, wherein said computational module performs correlation between said sample parameters and said reference parameters on a tuple basis, and determines said amount of lipid content based on best match between tuples corresponding to said sample parameters and said reference parameters.

18. The system according to claim 15, wherein said reference library comprises correlations between individual reference parameters and amount of lipid content.

19. The system according to claim 18, wherein said computational module performs correlation between said sample parameters and said reference parameters on an individual basis, and determines said amount of lipid content based on triangulation of a set of amounts of lipid content derived from individual reference parameters.

20. The system according to claim 15, wherein said reference library is indexed based on at least one or more of microalgal strains, cultivation media, and cell concentrations.

* * * * *